United States Patent [19]

Aleev et al.

[11] 4,165,750

[45] Aug. 28, 1979

[54] BIOELECTRICALLY CONTROLLED ELECTRIC STIMULATOR OF HUMAN MUSCLES

[76] Inventors: Leonid S. Aleev, ulitsa Semashko, 21, kv. 168; Sergei G. Bunin, ulitsa Vernadskogo, 67, kv. 76; Maya I. Vovk, ulitsa Oktyabrskoi revoljutsii, 16, kv. 70, all of Kiev; Vladimir N. Gorbanev, ulitsa Vasilkovskaya, 9, Fastov Kievskoi oblasti; Anatoly B. Shevchenko, ulitsa Ushinskogo, 11, kv. 64, Kiev; Fedor V. Balchev, ulitsa Zelenaya, 13, kv. 24, Vishnevy Kievskoi oblasti, all of U.S.S.R.

[21] Appl. No.: 885,082

[22] Filed: Mar. 9, 1978

[51] Int. Cl.² ............................................. A61N 1/36
[52] U.S. Cl. ................................................ 128/422
[58] Field of Search ............ 128/2.1 R, 2.1 M, 419 B, 128/419 PG, 419 R, 421, 422, 423 R

[56] References Cited

U.S. PATENT DOCUMENTS

| 2,368,207 | 1/1945 | Eaton | 128/422 |
| 3,593,718 | 7/1971 | Krasner et al. | 128/419 PG |
| 3,628,538 | 12/1971 | Vincent et al. | 128/422 |
| 3,650,277 | 3/1972 | Sjostrand et al. | 128/421 |
| 3,850,161 | 11/1974 | Liss | 128/422 |
| 3,866,600 | 2/1975 | Rey | 128/422 |

Primary Examiner—William E. Kamm
Attorney, Agent, or Firm—Steinberg & Blake

[57] ABSTRACT

A bioelectrically controlled electric stimulator of human muscles comprising an oscillator and a group of stimulator channels, each of the stimulator channels including a sensor for sensing the bioelectric activity of muscles of a programmer, a first integrator, a comparator, a modulator, a power amplifier, a unit for separating an electric signal, electrodes adapted to be connected to muscles of a person whose movement are under control, an amplifier of bioelectric activity of the person whose movements are under control and a second integrator connected to the output of the amplifier of bioelectric activity. The electric stimulator improves the correspondence between a movement performed by a person and a programmed movement. During the course of electric stimulation, pain is reduced and the stimulation signal is automatically correctable with respect to the functional state of the muscles being stimulated.

8 Claims, 57 Drawing Figures

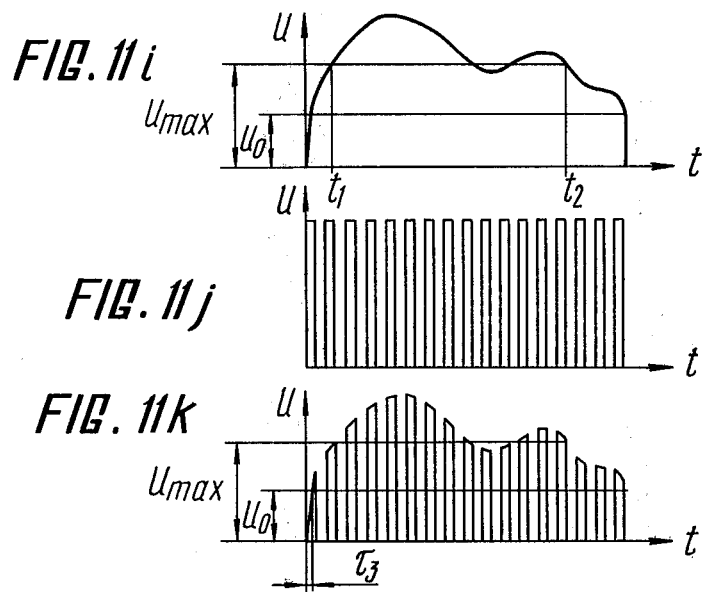

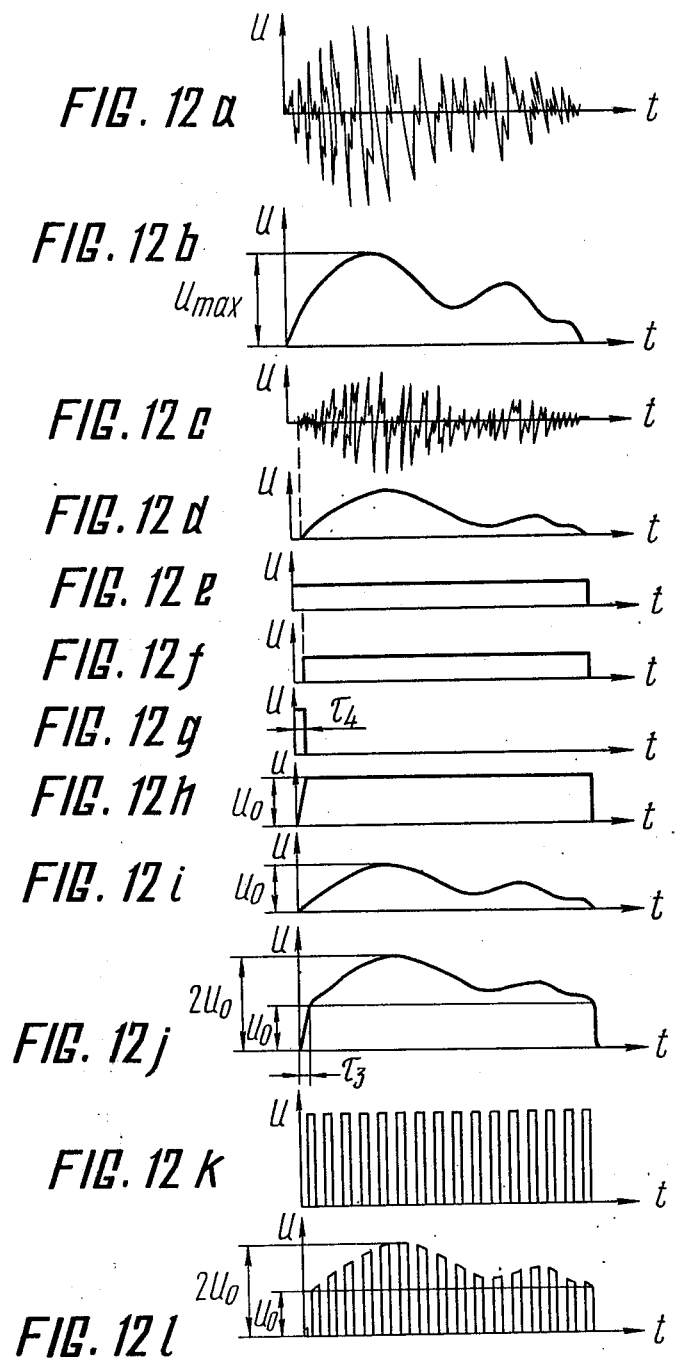

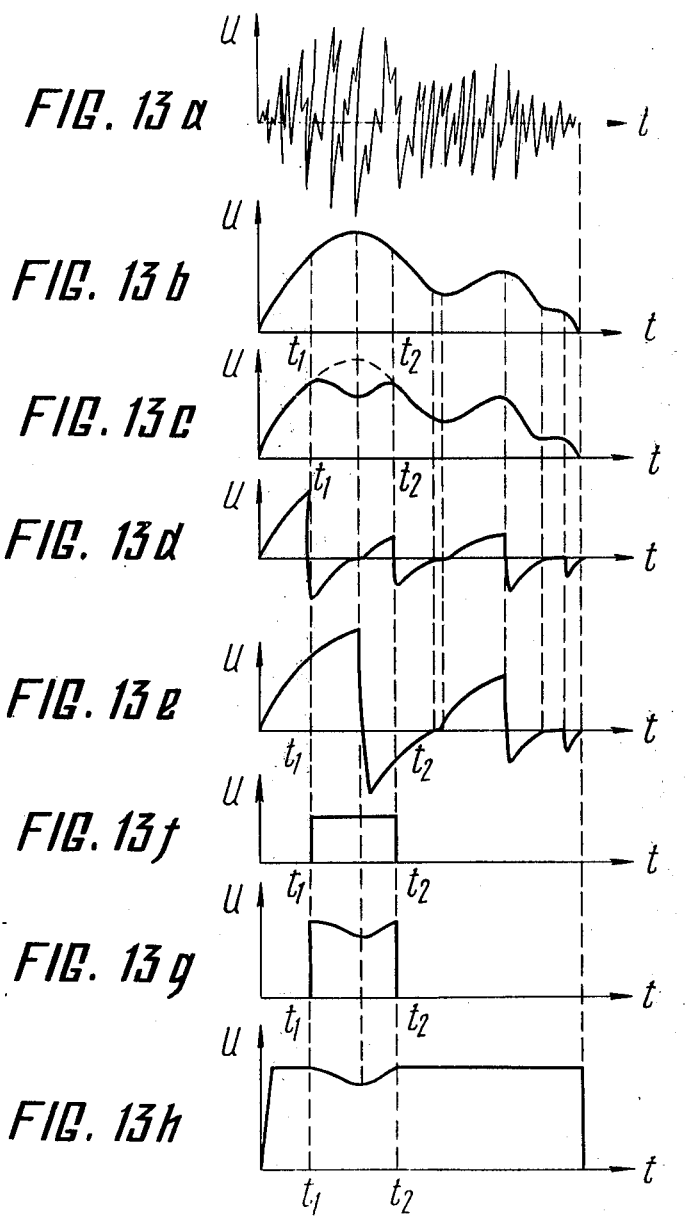

BIOELECTRICALLY CONTROLLED ELECTRIC STIMULATOR OF HUMAN MUSCLES

The present invention relates to medical equipment and, more particularly, to a bioelectrically controlled electric stimulator of human muscles.

The invention is applicable in clinical conditions for the analysis, diagnostics and treatment of dyskinesia of the central and peripheral origins. The invention is especially useful for treating neuritides of the facial, ulnar, radial, median, peroneal and tibial nerves, as well as residual disorders of cerebral circulation in the form of hemiplegia and hemiparesis, and residual disorders of poliomyelitis and infantile cerebral paralysis. The invention is also applicable to the control and correction of movements, as well as to mastering certain motor skills in the course of professional and sports training, etc. The invention can be used to the best advantage under special training conditions, when a person is in a state of hypokynesia or hypodynamia.

At present, the basic problem pertaining to electric stimulators of human muscles is how to use such stimulators not only for restoring the strength of damaged muscles, but also for restoring lost motor skills, i.e. how to enable a person to perform compound motions of the extremities, torso and head similar to those of a healthy person's extremities, torso and head.

The most promising type of electric stimulator is the bioeletrically controlled stimulator with a plurality of stimulation channels. In such stimulators, the control action on the output electric signal of the carrier frequency oscillator, which acts on human muscles, is provided by the bioelectric muscular activity of organs or tissues. Due to the fact that such stimulators have a plurality of channels and employ the bioelectric muscular activity of a person, who sets a program of movements, as the control action, such stimulators can electrically stimulate a plurality of muscles. The sequence of stimulation corresponds to the sequence of contractions of muscles in natural conditions, while performing certain movements. This provides for compound motions of the extremities, torso and head.

Of late, much attention has been paid to bioelectrically controlled electric stimulators incorporating a feedback system to provide information on the correspondence between a preset program of movements and the movements actually performed by a person.

The major difficulty in providing feedback systems for bioelectrically controlled electric stimulators is to develop sensors to supply information on the spatial position of the motor organs. There are different ways of solving this problem.

One of the solution is the use of what is known as the bioelectrolocation method which is carried out as follows. Electric stimulation brings about contraction of muscles, which is accompanied by bioelectric activity caused by the stimulating signal. The bioelectric activity can be registered with the aid of the same electrodes that are employed for muscle stimulation through the use of the time or frequency separation techniques. The response signal thus produced, i.e. the signal with which a muscle responds to stimulation, can be used as a feedback signal which provides information on the degree of correspondence between the actually performed and programmed movements and characterizes the functional state of the muscles being stimulated.

The foregoing principle of providing a feedback system for adjusting a signal which stimulates the muscular activity utilizes a bioelectrically controlled electric stimulator of human muscles, which comprises six stimulation channels. Each of said channels includes a bioelectric muscular activity sensor, which sets a program of movements, and a first integrator. The sensor and integrator are connected in series. The function of the bioelectric activity sensor can be performed by electrodes connected to human muscles and serving to register the bioelectric activity of these muscles, and a bioelectric activity amplifier. The bioelectric activity sensor can be constructed as a magnetic recorder which records the bioelectric activity data.

The output of the integrator is connected to the first input of a comparator for comparing the bioelectric muscular activity of a person who sets a program of movements and a person whose movements are under control. The integrator's output is also connected to the control input of a modulator. The other input of the modulator is connected to the output of an oscillator of the carrier frequency of the electric signal which stimulates the activity of muscles. This signal may be a sinusoidal or pulse electric signal. The output of the separator is connected to the input of said oscillator. The output of the modulator is coupled via a power amplifier to the first input of a unit for separating the electric signal, which stimulates muscular activity of the person whose movements are being controlled, and the bioelectric activity caused by said signal. The second input of said separation unit and its first output are connected to electrodes connected, in turn, to muscles of the person whose movements are under control. The second output of the separation unit is connected to a second integrator via an amplifier of bioelectric muscular activity of the person whose movements are under control. The output of the second integrator is connected to the second input of said comparator.

However, the bioelectrically controlled electric stimulator of human muscles under review cannot ensure complete correspondence between an actually performed movement and a programmed movement, which is due to the following factors.

In the known stimulator, the correspondence between the programmed and actually performed movements is achieved by adjusting one or several parameters of the signal which stimulates muscular activity (the stimulating signal). The adjustment equalizes the force and speed of contraction of muscles of the person who sets the program of movements and the person whose movements are under control. As a rule, several muscles take part in performing a movement. Thus, in order to ensure correspondence between the programmed and actually performed movements, the stimulating signal must be adjusted in each stimulation channel. As a result, it is necessary to have a stimulating signal carrier frequency oscillator in each channel, which accounts for a complicated design of the stimulator and causes pain in the course of stimulation. The pain is due to a low-frequency interference signal at the output of the oscillator; the interference, in turn, is caused by the combination frequencies of the oscillators of all the channels. Interference signals at the output of the oscillator can be avoided by synchronizing the stimulating signal frequencies of all the oscillators, in which case, however, the stimulator design becomes still more complicated.

In the final analysis, the actually performed movement is a far cry from the programmed one.

The lack of correspondence between the actually performed and programmed movements is also due to the fact that in the known stimulator, the program signal is applied through the electrodes to the muscles of the person, whose movements are being controlled, from zero level. It must be remembered in this connection that muscles show a strongly pronounced threshold effect, which means that they are excited and contract only at a certain level of the stimulating signal, referred to as the excitation threshold. As a stimulating signal is applied to the electrodes connected to muscles of a person whose movements are to be controlled, these muscles are excited and contract after some time lag relative to the construction of the respective muscles of the person setting the program of movements. The time lag is determined by the time required for the amplitude of the stimulating signal to reach the excitation threshold of the muscles of the person whose movements are under control, and depends on the speed of movement of the muscles at the initial moment of time. The greater the speed of the muscles' movement at the initial moment of time, the less the time lag and vice versa. As a result, the lack of correspondence between the actually performed and programmed movements is particularly pronounced if the person, who sets the program, performs slow movements.

In the known stimulator, another reason why the actually performed movements correspond but little to the programmed movements lies in the fact that the program signal is not adjusted to different functional states of different persons' muscles, as well as to changing functional states of muscles of one person, which states may vary in the course of electric stimulation.

It is known that there exist substantial differences in the functional state of muscles of different persons. This is especially true of pathological motor disturbances. The functional state of muscles being stimulated may also vary considerably in the course of electric stimulation. As a result, the dynamic range of the stimulating signal, within which the force or speed of contraction of muscles change linearly following a change in the signal's amplitude, is different in different persons, as well as in different muscles of one person in the course of stimulation. The dynamic range is to be understood as the range of the stimulating signal, which is limited from below by the amplitude of the stimulating signal, corresponding to the excitation threshold of the muscles of the person whose movements are under control and from above, by the maximum amplitude of said stimulating signal. The maximum amplitude of the stimulating signal is an amplitude whose further increase cannot linearly increase the force or speed of muscles' contraction.

It can be inferred from the above that it is necessary to adjust the dynamic range of the program signal with due regard for different functional states of muscles of different persons and changes in the functional state of muscles of one person during the stimulation process. It is also necessary to adjust the dynamic range of the program signal so that the maximum amplitude of the stimulating signal should not be in excess of a value at which stimulation brings pain.

In the known stimulator, the stimulating signal is adjusted without regard for the fatiguability of the muscles being stimulated, which invariably occurs in the course of electric stimulation. In order to avoid excessive strain of the neuromuscular system of a person being stimulated, it is necessary to discontinue the electric stimulation or switch over to sparing stimulation.

It is an object of the present invention to provide a bioelectrically controlled electric stimulator of human muscles, which would improve the correspondence between actually performed and programmed movements.

It is another object of the invention to mitigate pain in the course of stimulation.

It is still another object of the invention to make it possible to check the fatiguability of muscles in the course of electric stimulation and change the stimulation conditions at the onset of fatiguability.

It is yet another object of the invention to simplify the design and raise the reliability of the electric stimulator.

The objects of the present invention are attained by providing a bioelectrically controlled electric stimulator of human muscles, wherein each of at least two stimulation channels comprises in series a bioelectric muscular activity sensor, which sets a program of movements, and a first integrator electrically coupled with its output to the input of a comparator for comparing bioelectric muscular activity of a person who sets a program of movements with that of a person whose movements are under control, and to the control input of a modulator, to whose other input there is applied an electric signal stimulating the second person's muscles, the output of the modulator being electrically coupled to a power amplifier connected to the input of a unit for separating the electric signal, which stimulates muscles of the person whose movements are under control, and the bioelectric activity of these muscles, caused by said electric signal, the second input of said separation unit and its output being both connected to electrodes connected to muscles of the person whose movements are under control, the second output of the separation unit being coupled by means of an amplifier of bioelectric activity of muscles of the person, whose movements are under control, to a second integrator whose output is electrically coupled to the second input of the comparator for comparing the bioelectric activity of muscles of the person setting the program of movements with that of the person whose movements are under control, in which stimulator the output of the comparator for comparing the bioelectric activity of muscles of the person, who sets the program of movements, with that of the person, whose movements are under control, is electrically coupled, in accordance with the invention, to the control input of the modulator whose other input is connected to an oscillator of the carrier frequency of the stimulating electric signal, which oscillator is common for all the stimulation channels.

The proposed bioelectrically controlled electric stimulator of human muscles improves the degree of correspondence between actually performed and programmed movements, mitigates pain in the course of stimulation and features a simplified design.

It is expedient that the inputs of the comparator for comparing the bioelectric activity of muscles of the person, who sets the program of movements, with that of the person, whose movements are under control, should be directly connected to the respective outputs of the first and second integrators, whereas the output of the comparator should be connected to the control input of the modulator by means of an adder which must also be connected to the output of the first integrator. This makes it possible to reduce the time lag of a movement being performed with respect to a programmed movement and thus improve the correspondence between these movements.

It is also expedient that the inputs of the comparator for comparing the bioelectric activity of muscles of the person, who sets the program of movements, with that of the person, whose movements are under control, should be electrically coupled to the respective outputs of the first and second integrators by means of a first threshold element and a second threshold element, respectively, whereas the output of the comparator for comparing the bioelectric activity of muscles of the person, who sets the program of movements, with that of the person, whose movements are under control, should be electrically coupled to the control input of the modulator by means of a unit for forming the excitation threshold of muscles of the person, whose movements are under control, the input of said unit being connected to the output of the comparator and an adder whose input is electrically coupled to the output of said forming unit, its second input being electrically coupled to the output of the first integrator, whereas the second input of the unit for forming the excitation threshold of muscles of the person, whose movements are under control, is connected to the output of the first threshold element. This rules out a distortion of the program signal at the start of a movement and makes it possible to adjust the program signal with due regard for both the disparity in the actually performed and programmed movements, and the excitation threshold of the muscles being stimulated, which is dependent on the functional state of these muscles.

It is preferable that each stimulation channel should include a voltage divider whose input is connected to the output of the first integrator, the latter's control input being electrically coupled to the output of the unit for forming the excitation threshold of muscles of the person whose movements are under control, its output being connected to the second input of the adder. This makes it possible to adjust the dynamic range of program signals with due regard for the functional state of muscles of different persons, or to changes in the functional state of muscles of one person in the course of electric stimulation.

It is advisable that each stimulation channel should include a frequency meter and a first differentiator amplifier placed in series with the output of the amplifier of bioelectric activity of the person whose movements are under control, as well as a second differentiator amplifier whose input is connected to the output of the second integrator, a multiplier whose first input is connected to the output of the first differentiator amplifier, whereas its second input is connected to the output of the second differentiator amplifier, an electronic switch whose control input is connected to the output of the multiplier, whereas its other input is connected to the output of the frequency meter, and a second voltage divider whose control input is connected to the output of the electronic switch, its other input being connected to the output of the unit for forming the excitation threshold of muscles of the person whose movements are under control, whereas the output of said second voltage divider is connected to the control input of the first voltage divider. This makes it possible to form a stimulating signal with due regard for the fatiguability of muscles and either alter the stimulation conditions or discontinue the electric stimulation at a proper time and thus rule out excessive strain of the neuromuscular system of the person being stimulated.

It is also advisable that each stimulation channel should include a reference signal setting unit whose input is connected to the output of the first threshold element, a third threshold element, one of its inputs being connected to the output of the reference signal setting unit, its other input being connected to the output of the comparator for comparing the bioelectric activity of muscles of the person, who sets the program of movements, and the person, whose movements are under control, and a second electronic switch whose control input is connected to the output of the third threshold elements, its other input being connected to the output of the modulator, whereas its output is connected to the power amplifier. This accounts for an improved reliability of the stimulator and thus protects the person, whose movements are under control, from the effects of painful or dangerous electric signals.

Other objects and advantages of the present invention will be more readily understood from the following detailed description of preferred embodiments thereof to be read in conjunction with the accompanying drawings, wherein.

Figure 14A:
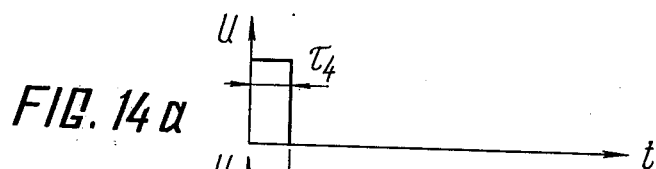
Figure 14B:
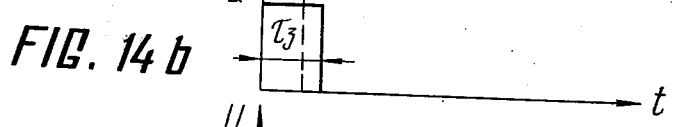
Figure 14C:
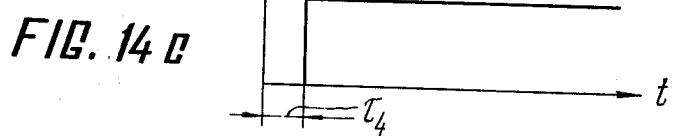

FIGS. 10 $a, b, c, d, e, f, g, h$ are time plots of electric signals at the outputs of the bioelectric activity sensor, the first integrator, the adder, the stimulating signal carrier frequency oscillator, the modulator, the bioelectric activity amplifier, the second integrator, and the comparator of bioelectric activity, respectively;

FIGS. 11 $a, b, c, d, e, f, g, h, i, j, k$ are time plots of electric signals at the outputs of the bioelectric activity sensor, the first integrator, the bioelectric activity amplifier, the second integrator, the first threshold element, the second threshold element, the comparator of bioelectric activity, the excitation threshold forming unit, the adder, the stimulating signal carrier frequency oscillator, and the modulator, respectively;

FIGS. 12 *a, b, c, d, e, f, g, h, i, j, k, l* are time plots of electric signals at the outputs of the bioelectric activity sensor, the first integrator, the bioelectric activity amplifier, the second integrator, the first threshold element, the second threshold element, the comparator of bioelectric activity, the excitation threshold forming unit, the first voltage divider, the adder, the stimulating signal carrier frequency oscillator, and the modulator, respectively;

FIGS. 13 *a, b, c, d, e, f, g, h, i, j, k, l, m, n* are time plots of electric signals at the outputs of the bioelectric activity amplifier, the second integrator, the frequency meter, the first differentiator amplifier, the second differentiator amplifier, the multiplier, the first electronic switch, the second voltage divider, the bioelectric activity sensor, the first integrator, the first voltage divider, the adder, the stimulating signal carrier frequency oscillator, and the modulator, respectively;

FIGS. 14 *a, b, c* are time plots of electric signals at the outputs of the reference signal setting unit, the comparator of bioelectric activity, and the third threshold element.

Figure 1:
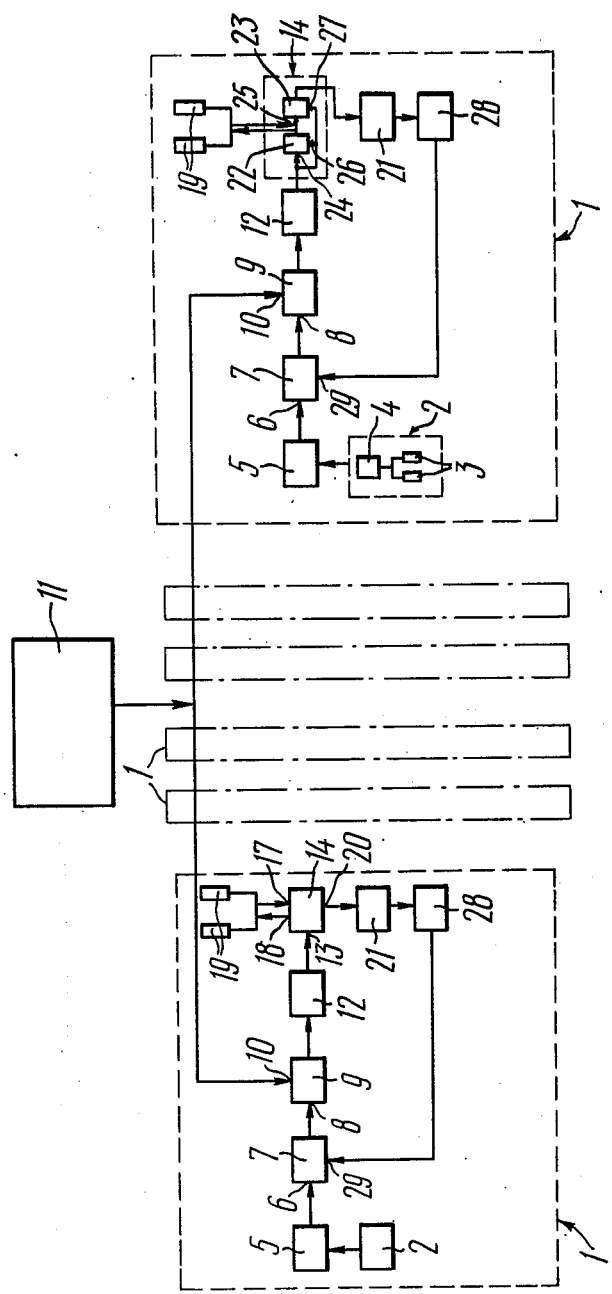
FIG. 1 is a block diagram of a bioelectrically controlled electric stimulator or human muscles, in accordance with the invention.

Referring to the attached drawings, the proposed bioelectrically controlled electric stimulator of human muscles comprises six stimulation channels 1 (FIG. 1). Each channel 1 includes a senser 2 of bioelectric activity of muscles, which sets a program of movements. As shown with reference to the sixth stimulation channel 1 of the proposed stimulator, the sensor 2 may comprise electrodes 3 connected to muscles (not shown) of a person who sets a program of movements, and also connected to a bioelectric activity amplifier 4 intended to amplify the bioelectric activity of muscles of said person. The electrodes 3 may be plates attached to the skin. Point or implantation electrodes can also be used. The bioelectric activity amplifier 4 is of the known type.

The bioelectric activity sensor 2 can be constructed as a memory, for instance, of the well-known magnetic recorder type.

The output of the bioelectric activity sensor 2 is connected to the input of an integrator 5. The integrator 5 comprises the well-known amplitude detector and integrating operational amplifier. The output of the integrator 5 is electrically coupled to an input 6 of a comparator 7 of the bioelectric activity of muscles of the person who sets the program of movements and that of a person whose movements are under control. The comparator 7 is conventionally built around an operational amplifier.

The output of the comparator 7 is electrically coupled to a control input 8 of a modulator 9 constructed as the well-known controlled voltage divider. An input 10 of the modulator 9 is connected to the output of an oscillator 11 of the carrier frequency of an electric signal which stimulates muscular activity. The oscillator 11 is common for all the channels 1. The oscillator 11 can be embodied as follows, depending on a desired type and shape of said electric signal.

If a sinusoidal electric signal is to be produced at the output of the oscillator 11, the latter may be constructed as the well-known master oscillator with LC circuits, or the well-known master oscillator built around RC elements.

If it is necessary to produce an electric signal in the form of unipolar pulses at the output of the oscillator 11, the latter comprises the well-known self-excited multivibrator and one-shot multivibrator placed in series.

The output of the modulator 9 is connected by means of a power amplifier 12 to an input 13 of a unit 14 for separating the electric signal which stimulates the muscular activity of the person whose movements are under control, and the bioelectric activity of that person's muscles, caused by said stimulating signal.

If a sinusoidal stimulating signal is used, the amplifier 12 is constructed as the known low-frequency amplifier with a transformer output.

In this case the separation unit 14 comprises serially connected filters 15 (FIG. 2) and 16. The filter 15 is the well-known symmetrical high-frequency filter, whereas the filter 16 is the well-known symmetrical low-frequency filter.

An input 17 (FIG. 1) and an output 18 of the separation unit 14 are connected to electrodes 19 connected to muscles of the person whose movements are under control. The electrodes 19 are similar to the electrodes 3. An output 20 of the separation unit is connected to the input of an amplifier 21 (FIG. 1) of bioelectric activity of muscles of the person whose movements are under control.

In case of using a pulse stimulating signal, the power amplifier 12 is the known pulse amplifier with a transformer output.

In this case the separation unit 14 comprises, as is shown with reference to the sixth channel 1 of the proposed stimulator, two serially placed electronic switches 22 and 23 of the known symmetrical type. An input 24 of the electronic switch 22 and an input 25 of the electronic switch 23 serve as the inputs 13 and 17, respectively, of the separation unit 14. The outputs of the electronic switches 22 and 23 are the outputs 18 and 20, respectively, of the separation unit 14. Control inputs 26 and 27 of the electronic switches 22 and 23, respectively, are connected to the input 24 of the electronic switch 22.

The bioelectric activity amplifier 21 is similar to the amplifier 4.

The output of the amplifier 21 is connected to the input of an integrator 28 which is similar to the integrator 5. The output of the integrator 28 is electrically coupled to an input 29 of the comparator 7 of bioelectric activity.

Figure 3:
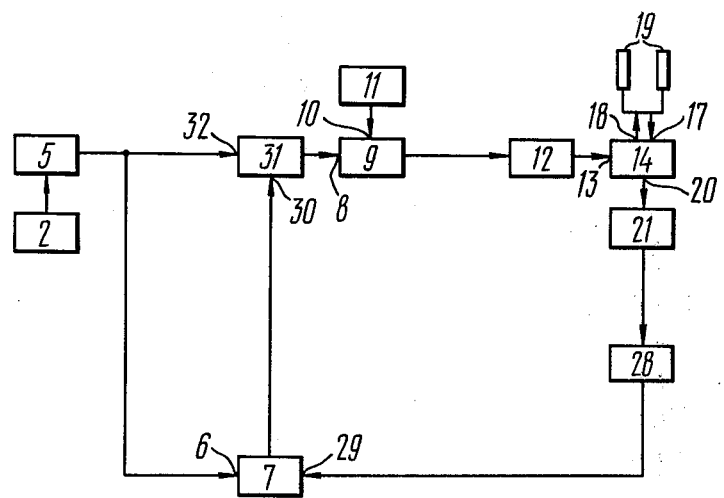
FIG. 3 is a block diagram of a stimulation channel with an adder of the electric stimulator in accordance with the invention.

FIG. 3 shows one stimulation channel of an electric stimulator which is similar to the one described above. The difference between the two embodiments is that in the latter case, the inputs 6 and 29 of the comparator 7 of bioelectric activity are directly connected to the outputs of the integrators 5 and 28, respectively. The output of the comparator 7 is connected to an input 30 of an adder 31. An input 32 of the adder 31 is connected to the output of the integrator 5. The output of said adder 31 is connected to the control input 8 of the modulator 9. The adder 31 is the known summing operational amplifier.

Figure 4:
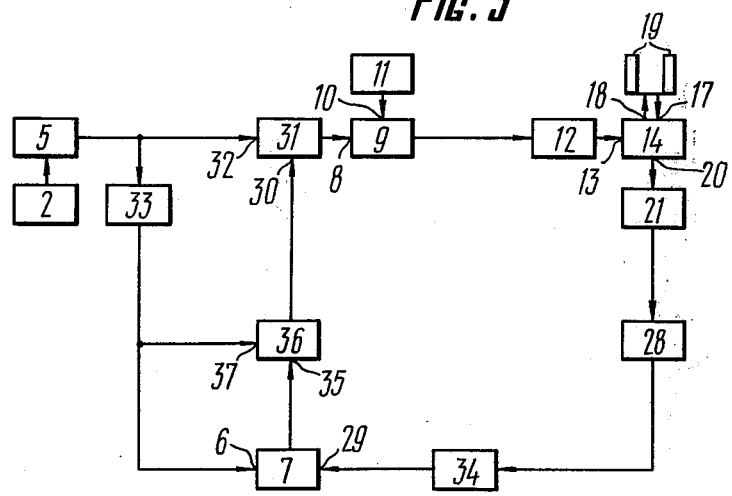
FIG. 4 is a block diagram of the stimulation channel of FIG. 3 with two threshold elements and a unit for forming the excitation threshold, in accordance with the invention.

FIG. 4 shows one channel of an electric stimulator similar to the one described above. However, unlike the embodiment of FIG. 3, the inputs 6 and 29 of the comparator 7 are connected to the outputs of the integrators 5 and 28 by means of respective threshold elements 33 and 34.

In this case the comparator 7 is the known flip-flop with separated inputs. The circuitry of the threshold elements 33 and 34 is that of the known operational amplifier.

The output of the comparator 7 is connected to an input 35 of a unit 36 for forming the excitation threshold of muscles of the person whose movements are under control. An input 37 of the unit 36 is connected to the output of the threshold element 33; the output of the unit 36 is connected to the input 30 of the adder 31. The excitation threshold forming unit 36 is the known capacitor storage.

Figure 5:
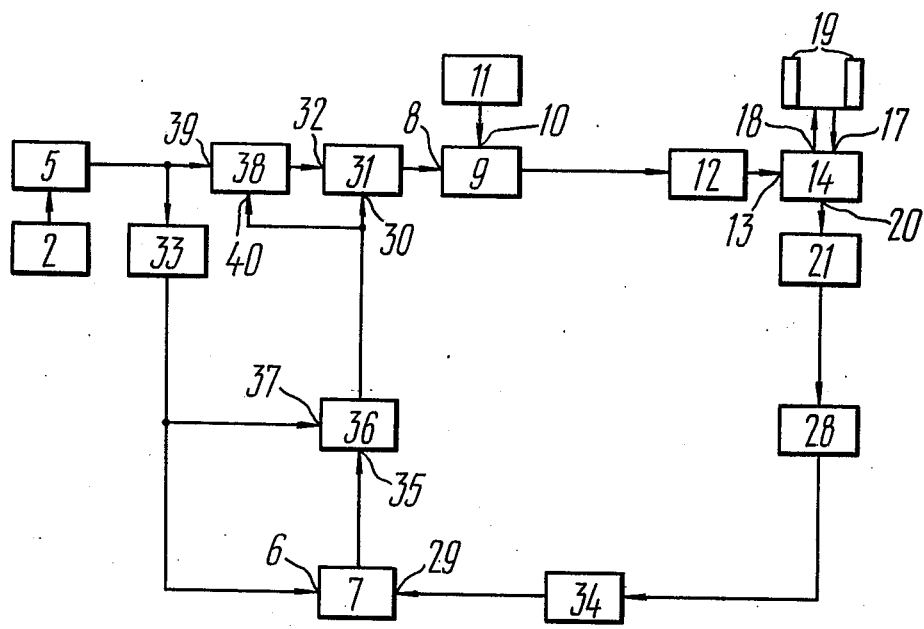
FIG. 5 is a block diagram of the stimulation channel of FIG. 4 with a voltage divider, in accordance with the invention.

Unlike the embodiment of FIG. 4, the electric stimulator, one of whose channels is shown in FIG. 5, comprises a conventional voltage divider 38. An input 39 of the voltage divider 38 is connected to the output of the integrator 5. A control input 40 of the voltage divider 38 is connected to the output of the excitation threshold forming unit 36.

Figure 6:
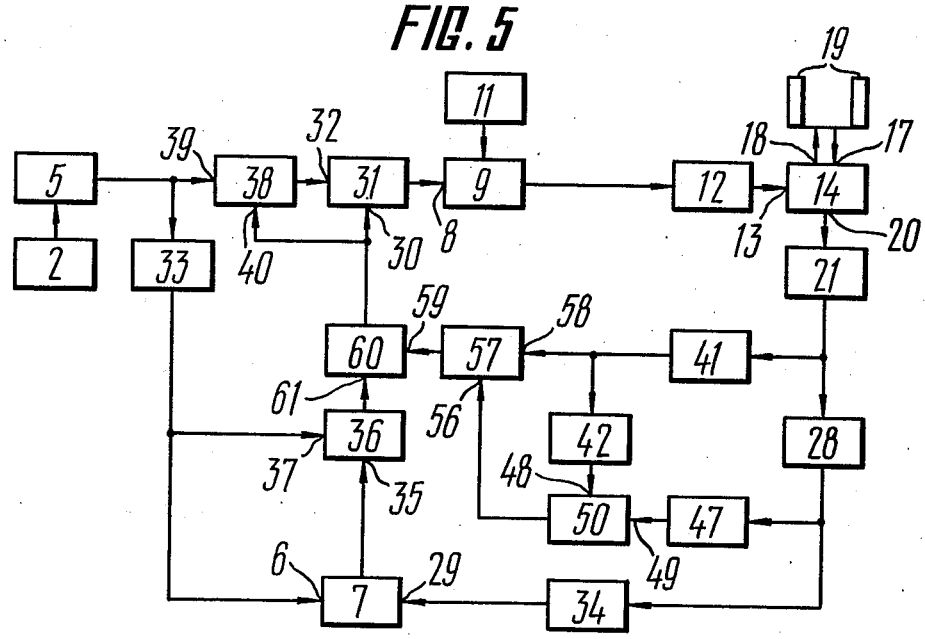
FIG. 6 is a block diagram of the stimulation channel of FIG. 5 with a frequency meter, differentiator amplifiers, a multiplier, an electronic switch, and a second voltage divider, in accordance with the invention.

Unlike the embodiment of FIG. 5, the electric stimulator, one of whose channels is shown in FIG. 6, comprises a frequency meter 41 whose input is connected to the output of the bioelectric activity amplifier 21. The output of the frequency meter 41 is connected to a differentiator amplifier 42.

The frequency meter 41 contains in series a limiter 43 (FIG. 7) of bioelectric muscular activity of the person whose movements are under control, a threshold element 44, a generator 45 of standard duration pulses, and an integrator 46.

The circuitry of the bioelectric activity limiter 43 is of the known type. The threshold element 44 is a Schmitt trigger. The generator 45 of standard duration pulses is a one-shot multivibrator. The integrator 46 and the differentiator amplifier 42 (FIG. 6) are of the known type.

Figure 8:
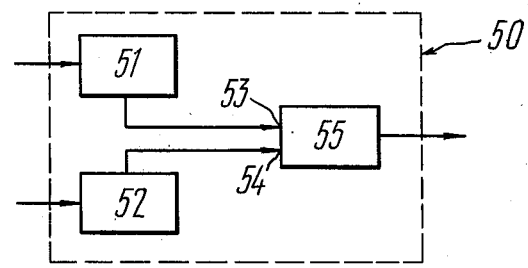
FIG. 8 is a structural diagram of the multiplier of the electric stimulator in accordance with the invention.

Connected to the output of the integrator 28 is a differentiator amplifier 47 which is similar to the differentiator amplifier 42. The outputs of the differentiator amplifiers 42 and 47 are connected to inputs 48 and 49, respectively, of a multiplier 50. The multiplier 50 comprises threshold elements 51 (FIG. 8) and 52 whose inputs are the inputs 48 (FIG. 6) and 49 of the multiplier 50, whereas their outputs are connected to respective inputs 53 (FIG. 8) and 54 of a logical AND circuit 55. The output of the logical AND circuit 55, which serves as the output of the multiplier 50 (FIG. 6), is connected to a control input 56 of an electronic switch 57. An input 58 of the electronic switch 57 is connected to the output of the frequency meter 41.

The threshold elements 51 (FIG. 8) are Schmitt triggers. The logical AND circuit 55 and the electronic switch 57 (FIG. 6) are of the known type.

Connected to the output of the electronic switch 57 is a control input 59 of a voltage divider 60 whose input 61 is connected to the output of the excitation threshold forming unit 36. The output of the voltage divider 60 is connected to the input 30 of the adder 31. The voltage divider 60 is similar to the voltage divider 38.

Figure 7:
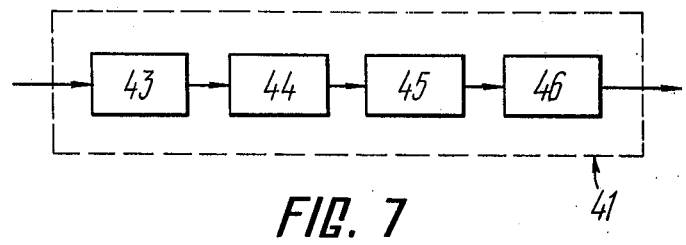
FIG. 7 is a structural diagram of the frequency meter of the electric stimulator in accordance with the invention.
Figure 9:
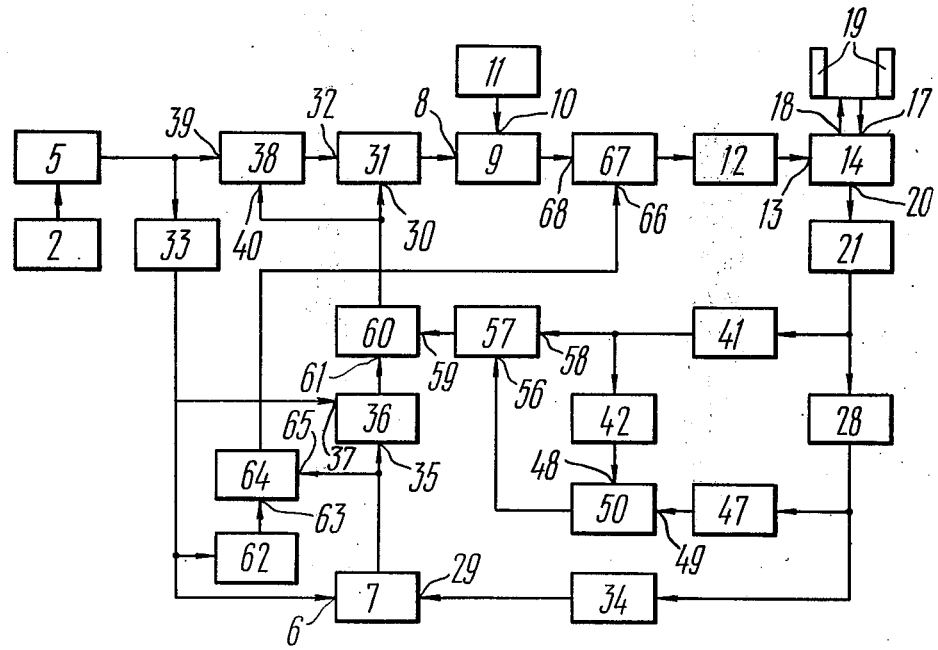
FIG. 9 is a block diagram of the stimulation channel of FIG. 6 with a reference signal setting unit, a third threshold element and a second electronic switch, in accordance with the invention.
Figure 10A:
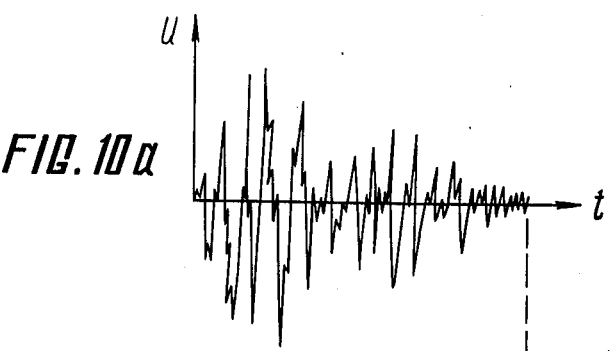
Figure 10B:
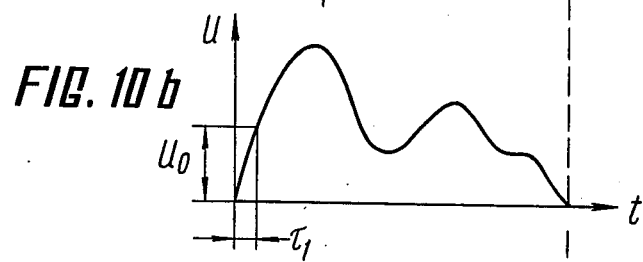
Figure 10C:
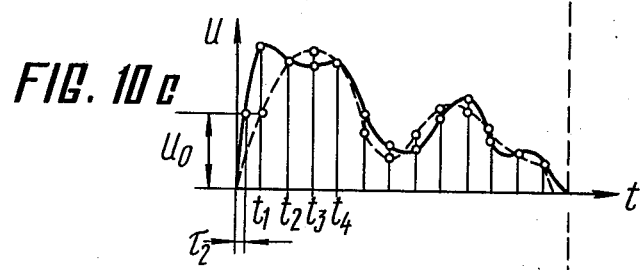
Figure 10D:
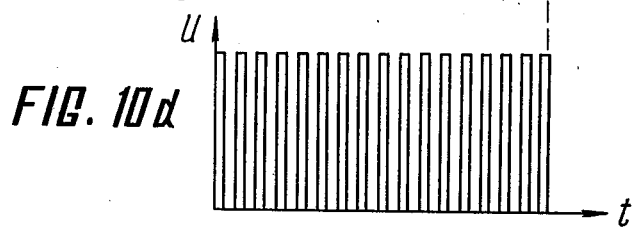
Figure 10E:
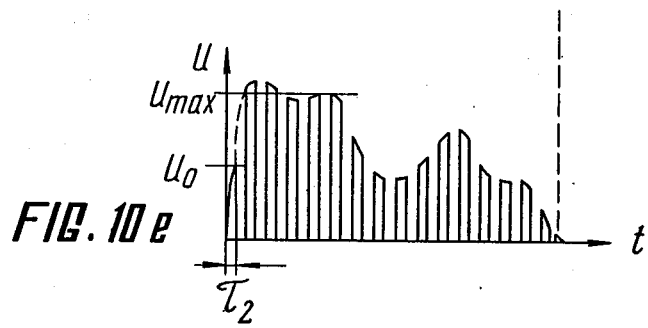
Figure 10F:
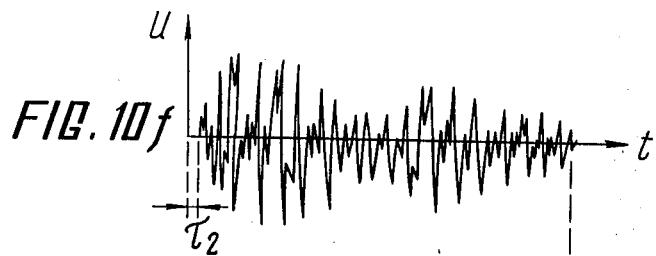
Figure 10G:
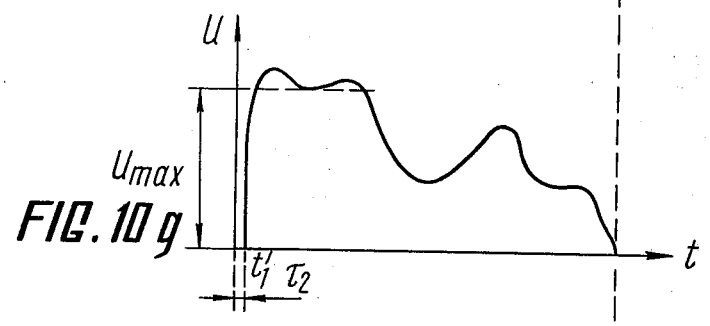
Figure 10H:
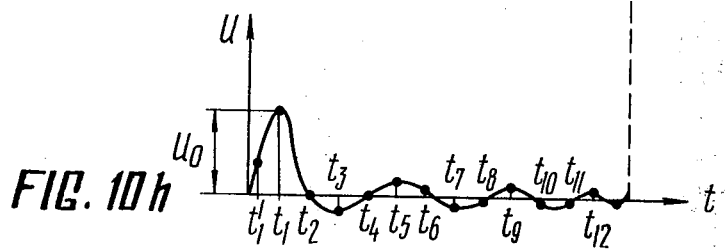
Figure 11A:
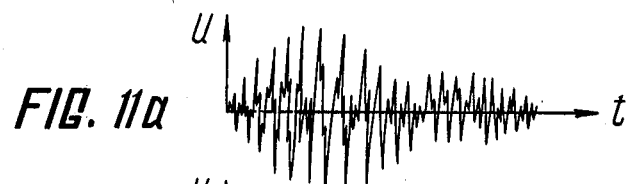
Figure 11B:
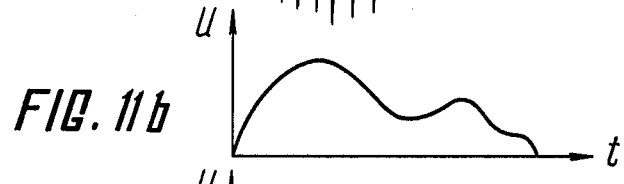
Figure 11C:
Figure 11D:
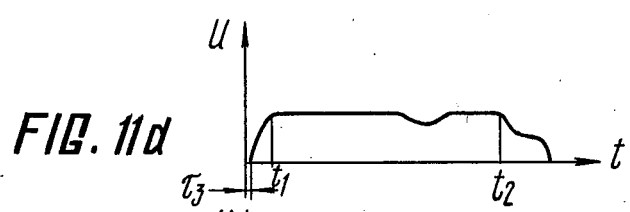
Figure 11E:
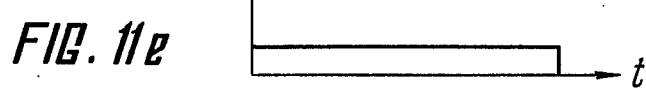
Figure 11F:
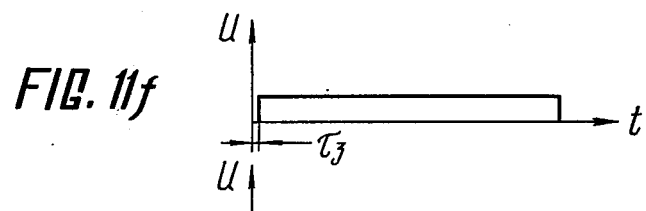
Figure 11G:
Figure 11H:
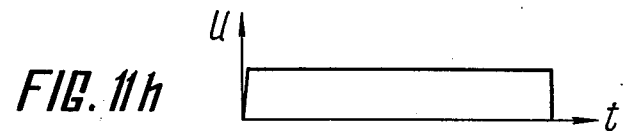
Figure 13I:
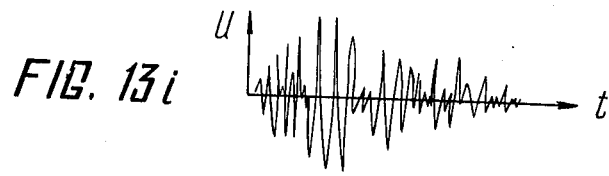
Figure 13J:
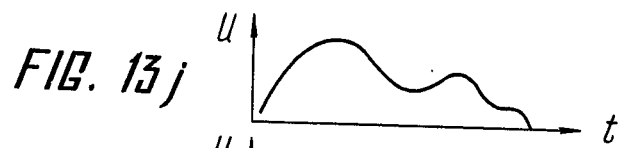
Figure 13K:
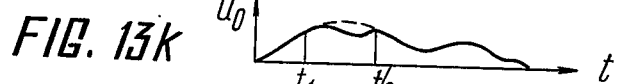
Figure 13L:
Figure 13M:
Figure 13N:
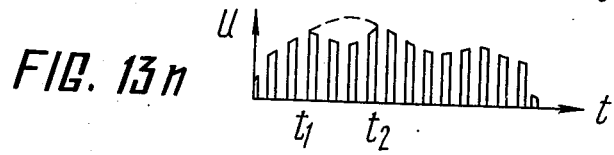

FIG. 9 shows one channel of an electric stimulator which is similar to the embodiment of FIG. 6. The difference between the two embodiments lies in the fact that in the latter case the stimulator includes a reference signal setting unit 62 whose input is connected to the output of the threshold element 33. The reference signal setting unit 62 is a standard duration pulse generator similar to the generator 45 (FIG. 7). Connected to the output of the reference signal setting unit 62 (FIG. 9) is an input 63 of a threshold element 64 which is the well-known logical AND circuit. An input 65 of the threshold element 64 is connected to the output of the comparator 7 of bioelectric activity. To the output of the threshold element 64 there is connected a control input 66 of an electronic switch 67. An input 68 of the electronic switch 67 is connected to the output of the modulator 9, whereas the output of the electronic switch 67 is connected to the power amplifier 12. The electronic switch 67 is similar to the electronic switch 57.

The known circuitries of the above-mentioned bioelectric activity amplifier 4 (FIG. 1), integrators 5, 28 and 46 (FIG. 7), comparator (FIG. 1) of bioelectric activity, oscillator 11, separation unit 14, adder 31 (FIG. 3), differentiator amplifiers 42 (FIG. 6) and 47, modulator 9, voltage divider 38, power amplifier 12, threshold elements 33 and 34, excitation threshold forming unit 36, limiter 43 (FIG. 7), generator 45, and reference signal setting unit 62 (FIG. 9) are described in the following sources: the article by Vodovnik and McLaud in the journal "Electronica", Moscow, 1965, pp. 32–39; N. G. Bruyevich, B. G. Dostupov, "Osnovy teorii schyotno-reshayushchikh ustroistv" /"Fundamentals of Computer Theory"/, Moscow, 1964, p. 249; "Spravochnik po radioelectronike" /"Handbook of Radio Electronics"/, ed. by A. A. Kulikovsky, Moscow, 1970, Vol. 3, pp. 285, 526, 97–200, 286; Aprikov, "Upravlyayemye deliteli nizkoi chastoty" /"Controlled Low Frequency Dividers"/, Moscow, 1969, p. 27; A. N. Starostin, "Impulsnaya technika" /"Pulse Engineering"/, Moscow, 1973, pp. 278, 288, 300, 175; R. S. Tsykin "Usilitelnye ustroistva" /"Amplifiers"/, Moscow, 1971, p. 141; B. A. Varshaver "Raschyot i proyektirovaniye impulsnykh usiliteley" /"The Calculation and Designing of Pulse Amplifiers"/, Moscow, 1975; "Spravochnik po telemetrii" /"Handbook of Telemetry"/, ed. by E. L. Grunberg, Moscow, 1971, p. 58; L. M. Goldberg, "Impulsnye i tsifrovye ustroistva" /"Pulse and Digital Devices"/, Moscow, 1973, pp. 240–265; I. M. Bolotin, V. A. Pavlenko, "Porogovye ustroistva dlya priborov avtomaticheskogo controlya i regulirovaniya" /"Threshold Devices for Automatic Control and Adjustment Equipment"/, Moscow, 1970, p. 6; M. I. Gryaznov, M. A. Gurvich, Z. V. Mograchyov, "Izmereniye impulsnykh napryazheniy" /"Pulse Voltage Measurement"/, Moscow, pp. 134–149; I. S. Itskhoki, N. I. Ovchinnikov, "Impulsnye i tsifrovye ustroistva" /"Pulse and Digital Devices"/, Moscow, 1972, p. 509).

For better understanding of the operation of the proposed electric stimulator, FIGS. 10 *a, b, c, d, e, f, g, h,* show time plots of electric signals at the outputs of the bioelectric activity sensor 2 (FIG. 1), the integrator 5, the adder 31 (FIG. 3), the stimulating signal carrier frequency oscillator 11, the modulator 9, the bioelectric activity amplifier 21, the integrator 28, and the comparator 7 of bioelectric activity, respectively.

FIGS. 11 *a, b, c, d, e, f, g, h, i, j, k* are time plots of electric signals at the outputs of the bioelectric activity sensor 2 (FIG. 4), the integrator 5, the bioelectric activity amplifier 21, the integrator 28, the threshold element 33, the threshold element 34, the comparator 7, the excitation threshold forming unit 36, the adder 31, the stimulating signal carrier frequency oscillator 11, and the modulator 9, respectively.

FIGS. 12 *a, b, c, d, e, f, g, h, i, j, k, l* are time plots of electric signals at the outputs of the bioelectric activity sensor 2 (FIG. 5), the integrator 5, the bioelectric activity amplifier 21, the integrator 28, the threshold element 33, the threshold element 34, the comparator 7, the excitation threshold forming unit 36, the voltage divider 38, the adder 31, the stimulating signal carrier frequency oscillator 11, and the modulator 9, respectively.

FIGS. 13 a, b, c, d, e, f, g, h, i, j, k, l, m, n are time plots of electric signals at the outputs of the bioelectric activity amplifier 21 (FIG. 6), the integrators 28, the frequency meter 41, the differentiator amplifier 42, the differentiator amplifier 47, the multiplier 50, the electronic switch 57, the voltage divider 60, the bioelectric activity sensor 2, the integrator 5, the voltage divider 38, the adder 31, the stimulating signal carrier frequency oscillator 11, and the modulator 9, respectively.

FIGS. 14 a, b, c are time plots of electric signals at the outputs of the reference signal setting unit 62 (FIG. 9), the comparator 7, and the threshold element 64.

In the above-mentioned time plots, time t is plotted as abscissas, and the amplitude U of electric signals is plotted as ordinates. The amplitude $U_o$ is equal to a stimulating signal amplitude corresponding to the excitation threshold of muscles being stimulated. The amplitude $U_{max}$ corresponds to a maximum amplitude of the stimulating signal.

The foregoing embodiments of the proposed bioelectrically controlled electric stimulator of human muscles operate as follows.

When the sensor 2 (FIG. 1) comprises the serially connected electrodes 3 connected to muscles of the person, who sets a program of movements, and the amplifier 4, the bioelectric activity is directly picked with the aid of the electrodes 3 of each stimulation channel 1 (FIG. 1) off these muscles, as the person performs a movement. The bioelectric activity is amplified by the amplifier 4 so that at the output of the sensor 2 there is produced an amplified version of the bioelectric activity of the person who sets the program of movements. In case of using the electrodes 3 of the surface type, the bioelectric activity is represented as the electric signal of FIG. 10 a.

When the sensor 2 is a magnetic recorder, from this sensor there is taken the prerecorded and preamplified bioelectric activty of muscles of the person who sets the program of movements, which is represented as the electric signal of FIG. 10 a.

From the output of the bioelectric activity sensor 2, the electric signal is applied to the input of the integrator 5 intended the separate the useful information on the programmed movement from said signal. The integrator 5 detects and integrates the electric signal. At the output of the integrator 5 there is produced the program electric signal shown in FIG. 10 b. This signal represents the time-averaged bioelectric activity of muscles of the person who sets the program of movements. From the output of the integrator 5, this electric signal is applied to the input 6 of the comparator 7 of bioelectric activity. At an initial period of time $\tau_1$ (FIG. 10 b), there is no electric signal carrying information on the performed movement at the input 29 of the comparator 7, because the stimulating signal has not yet reached the excitation threshold $U_o$ of the muscles being stimulated. Therefore, during this period of time at the output of the comparator 7 there appears an electric signal whose shape and amplitude coincide with those of the signal applied to the input 6 of said comparator 7. This signal is shown in FIG. 10 b.

From the output of the comparator 7, the electric signal is applied to the control input 8 of the modulator 9. From the output of the stimulating signal carrier frequency oscillator 11 to the input 10 of the modulator 9 there is applied a stimulating electric signal. The signal is applied in the form of unipolar square pulses shown in FIG. 10 d. In order to reduce pain and increase the force of contraction of the muscles being stimulated, it is advisable that the duration of pulses should be 0.1 to 0.5 msec, whereas the pulse repetition frequency should be 80 to 200 Hz. The function of the stimulating signal can also be performed by bipolar square pulses or a sinusoidal signal whose frequency is selected to be equal to 2 to 5 khz for the above reasons.

The use of sinusoidal electric signals at frequencies of 2 to 5 Hz for electric stimulation is due to the fact that they are less painful than other electric signals.

The modulator 9 converts the stimulating electric signal shown in FIG. 10 d so that at its output there is produced an electric signal whose type and shape coincide with those of the stimulating signal, i.e. a sequence of square pulses whose amplitude changes with time as the amplitude of the program signal. From the output of the modulator 9, the converted stimulating signal is applied to the input of the power amplifier 12 and is amplitude-amplifier to a level required for stimulation. Then, the signal is applied via the separation unit 14 to the electrodes 19 connected to the muscles being stimulated.

If at the output of the oscillator 11 there is formed the stimulating pulse signal shown in FIG. 10 a, the converted stimulating signal is applied from the output of the power amplifier 12 via the electronic switch 22 (FIG. 1) to the electrodes 19 connected to the muscles of the person whose movements are under control. As a result, these muscles are excited and contract. During time intervals between the pulses, the resultant bioelectric activity of the muscles being stimulated is applied via the electronic switch 23 to the input of the bioelectric activity amplifier 21.

During the action of the stimulating signal pulses, the electronic switch 22 is conducting, and the stimulating signal is applied to the electrodes 19. Meanwhile, the electronic switch 23 is not conducting, and the stimulating signal is not applied to the input of the bioelectric activity amplifier 21. During the intervals between the stimulating signal pulses the electronic switch 22 is not conducting, and the intrinsic noise of the power amplifier 12 cannot reach the input of the bioelectric activity amplifier 21. Meanwhile, the electronic switch 23 is conducting, and the bioelectric activity of the muscles being stimulated is applied from the output of the electrodes 19 to the input of the amplifier 21.

Figure 2:
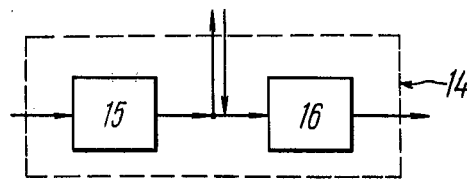
FIG. 2 is a structural diagram of the unit for separating the electric signal, which stimulates muscles of the person whose movements are under control, and the bioelectrical activity of these muscles of the electric stimulator in accordance with the invention.

If a sinusoidal stimulating signal is formed at the output of the oscillator 11, the frequency separation of this signal from the bioelectric activity of the muscles being stimulated, carried out by the separation unit 14 constructed as shown in FIG. 2, is made possible due to the fact that the range of bioelectric activity of muscles, which includes frequencies of 0 to 800 Hz, is much lower than the stimulating signal frequency. In this case the stimulating signal is applied from the output of the power amplifier 12 via the high-frequency filter 15 (FIG. 2) to the electrodes 19 connected to the muscles being stimulated. As a result, the muscles being stimulated are excited and contract. The electrodes 19 pick up the resultant bioelectric activity which is applied via the low-frequency filter 16 (FIG. 2) to the input of the bioelectric activity amplifier 21 (FIG. 1).

The low-frequency filter 16 (FIG. 2) performs the basic function of separating the sinusoidal stimulating signal having a frequency of 5 Hz, for example, from the bioelectric activity of the muscles being stimulated. It is desirable that the transmission band of the filter 16 should be 0 to 800 Hz, because the maximum bioelectric activity of the muscles being stimulated is found within this frequency band.

The high-frequency filter 15 is intended to avoid the inclusion of the intrinsic noise of the power amplifier 12 (FIG. 1), whose frequency is within the bioelectric activity frequency band, in the bioelectric activity of the muscles being stimulated. The filter 15 (FIG. 2) also serves to correlate the output resistance of the power amplifier 12 with the inter-electrode resistance of the tissues being stimulated and remove the bioelectric activity from these tissues.

It is advisable that the cutoff frequency of the high-frequency filter 15 should be somewhat lower than the frequency of the stimulating signal. For example, at a frequency of the stimulating signal of 5 khz, the cutoff frequency of the filter 15 should be 4 khz.

From the output of the amplifier 21 (FIG. 1), the bioelectric activity of the muscles being stimulated is applied to the input of the integrator 28. As the integrator 5, the integrator 28 separates the useful information on the movement performed by the person whose muscles are being stimulated.

At the output of the integrator 28, there is produced an electric signal which is the time-averaged bioelectric activity of the muscles being stimulated and carries information on the movement being performed. This information signal is applied to the input 29 of the comparator 7, to whose input 6 there is applied a program signal from the output of the integrator 5.

The comparator 7 compares the instantaneous amplitude values of the program signal with those of the information signal. At the output of the comparator 7 there is produced a signal which adjusts the program signal, depending on the type of electric coupling between the output of the comparator 7 and the control input 8 of the modulator 9, which types are described below, with reference to other preferred embodiments of the proposed electric stimulator. The correction of the program signal ensures correspondence between the actually performed and programmed movements.

The corrected program signal is applied to the control input 8 of the modulator 9, to whose input 10 there is applied the stimulating signal from the oscillator 11. At the output of the modulator 9 there is formed a stimulating signal converted in accordance with the corrected program signal. This signal is amplified by the amplifier 12 and applied via the separation unit 14 to the electrodes 19 and to the muscles being stimulated. The signal ensures correspondence between contractions of these muscles and contractions of the same muscles of the person setting the program of movements.

The operation of the stimulator of FIG. 3 is similar to that of the stimulator of FIG. 1. The difference is that in each stimulation channel 1 (FIG. 1), the program signal shown in FIG. 10 b is applied from the output on the integrator 5 to the input 6 of the comparator 7 and to the input 32 ( FIG. 3) of the adder 31. During the initial period of time $\tau_1$ (FIG. 10 b), the amplitude of the program signal and, consequently, the amplitude of the stimulating signal do not reach $U_o$ corresponding to the excitation threshold of the muscles being stimulated; there is no signal at the input 29 of the comparator 7. As a result, at the output of the comparator 7 there is produced a program signal shown in FIG. 10 b. This program signal is applied to the input 30 of the adder 31. Within the period of time from 0 to $t_1$, at the output of the adder 31 there is produced the electric signal shown in FIG. 10 c. The amplitude of this signal is double the amplitude of the program signal shown in FIG. 10 c by the dash line.

From the output of the adder 31, this signal is applied to the input 8 of the modulator 9. The modulator 8 converts the stimulating signal shown in FIG. 10 d so that its output there is produced the signal shown in FIG. 10 e. This signal is a sequence of unipolar square pulses shown in FIG. 10 d, whose amplitude changes with time in accordance with the change in the program signal shown in FIG. 10 c.

It is clear from the above and from the time plots of FIGS. 10 c and 10 e that due to the presence of the multiplier 31, the amplitude of the converted stimulating signal reaches the value of $U_o$, which corresponds to the excitation threshold of the muscles being stimulated not as the amplitude of the program signal does, i.e. during the period of time $\tau_1$, but two times faster, i.e. during the period of time $\tau_2$ (FIG. 10 e). As a result, the time lag between the appearance of the program signal and the onset of bioelectric activity of the muscles being stimulated, shown in FIG. 10 f, is reduced about one half and is equal to $\tau_2$.

As the information signal shown in FIG. 10 g appears at the output of the integrator 28 and as this signal is applied to the input 29 of the comparator 7, at the output of said comparator 7 there appears during the period of time $(t_1-t_2)$ (FIG. 10 h) a correction signal whose amplitude at any moment of time is equal to the difference between the instantaneous amplitude values of the program signal and the information signal. The adder 31 (FIG. 3) adds this correction signal to the program signal applied to its input 32, which decreases the value of the signal at its output, as shown in FIG. 10 c. This results in a distortion of the amplitude-time relationship between the output signal of the adder 31 and the program signal at its input 32. The distortion manifests itself in that an increase in the amplitude of the program signal during the period of time $(t_1-t_2)$ (FIG. 10 c) is accompanied by a decrease in the amplitude of the signal at the output of the adder 31 (FIG. 3). This occurs until the instantaneous value of the program signal amplitude is equal to that of the information signal. In this case at the moment of time $t_2$ (FIG. 10 h), the amplitude of the signal at the output of the comparator 7 is zero, whereas at the output of the adder 31 (FIG. 5) it is equal to the instantaneous value of the amplitude of the program signal at its input 32. This means that at the moment of time $t_2$ (FIG. 10 c) the adder 31 (FIG. 5) does not correct the program signal.

During the period of time that follows, overcompensation occurs due to the time lag of the system, and there may come a moment when the instantaneous amplitude value of the information signal is in excess of that of the program signal.

In this case a negative correction signal appears at the output of the comparator 7 during the period of time $(t_2-t_3)$ (FIG. 10 h). The adder 31 (FIG. 3) adds this signal to the program signal, whereby the amplitude of the signal at the output of the adder 31, shown in FIG. 10 c, is reduced by a value which is equal to the difference between the instantaneous amplitude values of the program and information signals.

The processes which take place during the period of time $(t_3-t_4)$ (FIG. 10 h) are reversed, as compared to the processes that take place during the period of time $(t_2-t_3)$. During this period of time, the output signal of the adder 31 (FIG. 3), shown in FIG. 10 c, increases in amplitude, as compared to the program signal shown in FIG. 10 c by the dash line. Thus, the program signal is corrected again to ensure correspondence between the instantaneous amplitude values of the program and information signals.

The fact that the time lag $\tau_2$ of the information signal relative to the program signal is reduced by half, as compared to the known stimulator described above, accounts for an improved correspondence between the actually performed and programmed movements. However, this is only true of the steady-state operating conditions, i.e. during the periods of time $(t_2-t_{13})$ (FIG. 10 h).

The operation of the electric stimulator of FIG. 4 is similar to that of the stimulator of FIG. 3. The difference is that in each stimulation channel 1 (FIG. 1), the program signal is applied from the output of the integrator 5 to the input of the threshold element 33 (FIG. 4), at whose output there is formed a square pulse of a constant amplitude, shown in FIG. 11 e. The duration of this pulse is determined by that of the program signal at the output of the integrator 5. The square pulse is applied to the input 37 of the excitation threshold forming unit 36 and the input 6 of the comparator 7.

The information signal shown in FIG. 11 d is applied from the output of the integrator 28 to the input of the threshold element 34 after a time lag $\tau_3$ (FIG. 11 d) relative to the program signal. At this moment, at the output of the threshold element 34 there is produced a square pulse shown in FIG. 11 f, which is applied to the input 29 of the comparator 7. At the latter's output there is produced a square pulse of a constant amplitude, shown in FIG. 11 g, whose duration is equal to the time lag $\tau_3$ of the information signal relative to the program signal. The time lag is proportional to the excitation threshold of the muscles being stimulated, so the duration of this pulse corresponds to the excitation threshold. From the ouput of the comparator 7 the square pulse is applied to the input 35 of the excitation threshold forming unit 36, to whose input 37 there is applied, as is mentioned above, the square pulse shown in FIG. 11 e. At the output of the unit 36 there is produced a pulse shown in FIG. 11 h, which exponentially rises during the period of time $\tau_3$. The amplitude of this pulse is proportional to the duration of the pulse shown in FIG. 11 g, i.e. to the excitation threshold of the muscles being stimulated. The duration of this pulse is determined by the duration of the pulse shown in FIG. 11 e, which means that it is determined by the duration of the program signal shown in FIG. 11 b. The rate of rise of the pulse at the output of the excitation threshold forming unit 36 is selected and adjusted with reference to a minimum of pain caused by the electric stimulation. At the same time it is advisable that the rate of rise should be one order higher than the maximum rate of change in the program signal.

The pulse formed at the output of the unit 36 serves as the correction signal and is applied to the input 30 of the adder 31. At the latter's output there is produced an electric signal shown in FIG. 11 i. The amplitude of this signal is equal to the sum total of the amplitudes of the program signal and the correction signal corresponding to the excitation threshold of the muscles being stimulated. The corrected program signal is applied to the input 8 of the modulator 9, to whose input 10 there is applied the stimulating signal in the form of square pulses shown in FIG. 11 j. At the output of the modulator 9 there is produced a converted stimulating signal shown in FIG. 11 k. At each moment of time, the amplitude of this signal is equal to the sum total of the amplitudes of the program signal and the correction signal.

As a result, the electric signal is applied to the muscles not from the zero level, but from a level equal to the excitation threshold of the muscles being stimulated, which considerably reduces the time lag of the information signal relative to the program signal. The time lag is only determined by the time of rise of the pulse at the input of the excitation threshold forming unit 36.

The stimulator of FIG. 5 operates in a manner similar to the operation of the stimulator of FIG. 4. The difference is that in the latter case in each stimulation channel 1 (FIG. 1), the program signal shown in FIG. 12 b, which is produced at the onset of a prescribed bioelectric activity shown in FIG. 12 a, is applied from the output of the integrator 5 not only to the input of the threshold element 33 (FIG. 5), but also to the input 39 of the voltage divider 38. To the input 40 of said voltage divider 38 from the output of the excitation threshold forming unit 36 there is applied a correction signal in the form of an exponentially rising pulse shown in FIG. 12 h. This pulse adjusts the transfer ratio of the voltage divider 38 so that at the latter's output the amplitude of the converted program signal is not in excess of $(K-1) \cdot U_o$, where $U_o$ is the amplitude of the correction signal, corresponding to the excitation threshold of the muscles being excited. The foregoing amplitude ratio is selected for the following reasons.

The maximum amplitude $U_{max}$ of the converted stimulating signal is related to the excitation threshold of the muscles being stimulated through the proportionality factor K. Therefore, in order to ensure the amplitude of the converted stimulating signal is not in excess of a maximum value, it is necessary that the maximum amplitude of the program signal, added to the amplitude of the correction signal, which corresponds to the excitation threshold of the muscles being stimulated, should not be in excess of the maximum amplitude of the converted stimulating signal. This means that the maximum amplitude of the converted program signal must not be in excess of $(K-1) \cdot U_o$. This is taken care of by the voltage divider 38.

At the output of the voltage divider 38 there is formed a converted program signal shown in FIG. 12 i, whose maximum amplitude is not greater than $U_o$.

In the time plots of FIG. 14, K=2, which means that the maximum amplitude of the converted program signal is not in excess of a value corresponding to the excitation threshold of the muscles being stimulated.

From the output of the voltage divider 38, the converted program signal is applied to the input 32 of the adder 31, to whose input 30 there is applied a correction signal whose amplitude is proportional to the excitation threshold of the muscles being stimulated. At the output of the adder 31 there is produced a corrected program signal shown in FIG. 12 j, whose amplitude at any moment of time is equal to the sum total of the amplitudes of the above-mentioned signals applied to the inputs 30 and 32 of said adder 31. The maximum amplitude of this signal is not in excess of double the frequency corresponding to the excitation threshold of the muscles being stimulated. This signal is applied to the control input 8 of the modulator 9, to whose input 10 there is applied the stimulating signal in the form of pulses shown in FIG. 12 k.

At the output of the modulator 9, there is produced a converted stimulating signal shown in FIG. 12 l. The minimum value of the amplitude of this signal is equal to $U_o$ corresponding to the excitation threshold of the muscles being stimulated, whereas its maximum value is equal to $2U_o$. Thus the electric signal is applied to the muscles being stimulated from a level corresponding to the excitation threshold of these muscles, and the maximum amplitude of this signal is not greater than the maximum amplitude of the stimulating signal for these muscles. As a result, the person whose muscles are being stimulated feels less pain and the muscles which are being stimulated are excited and contract in accordance with the excitation and contraction of the muscles of the person who sets the program of movements; the actually performed movement corresponds more fully to the programmed movement.

In the course of electric stimulation, the excitation threshold of the muscles being stimulated varies (as a rule, it rises); consequently, the amplitude of the converted stimulating signal applied to the muscles is also changed. It follows that during the stimulation process the dynamic range of the program signal shown in FIG. 12 b is adjusted to the changing functional state of the muscles of one person, or different functional states of muscles being stimulated of different persons.

The operation of the stimulator shown in FIG. 6 is similar to that of the stimulator of FIG. 5. The difference is that in each stimulation channel 1 (FIG. 1), the electric signal shown in FIG. 13 a is applied from the output of the bioelectric activity amplifier 21 to the input of the integrator 28 and the input of the frequency meter 41 (FIG. 6). At the output of the frequency meter 41 there is produced an electric signal shown in FIG. 13 c, whose amplitude is proportional to the mean bioelectric activity frequency of the muscles being stimulated at a given moment of time. From the output of the frequency meter 41, this signal is applied to the input of the differentiator amplifier 42, at whose output there is produced an electric signal shown in FIG. 13 d. At any moment of time the amplitude of this signal is proportional to the rate of change of the mean bioelectric activity frequency of the muscles being stimulated.

If at a given moment the mean bioelectric activity frequency is increasing, this signal is positive; if the mean frequency decreases, the signal is negative. The signal is positive or negative polarity is applied to the input 48 of the multiplier 50.

From the output of the integrator 28, the time-averaged bioelectric activity of the muscles being stimulated, shown in FIG. 13 b, is applied to the input of the differentiator amplifier 47 at whose output there is formed a signal shown in FIG. 13 e. The amplitude of this signal is proportional to the rate of change of the amplitude of the time-averaged bioelectric activity of the muscles being stimulated. This signal may be of positive or negative polarity, depending on whether the amplitude of the signal applied to the input of said differentiator amplifier 47 increases or decreases at a given moment of time. The signal is applied to the input 49 of the multiplier 50. At the output of said multiplier 50 there is produced a square pulse shown in FIG. 13 f; this occurs only within the period of time ($t_1$-$t_2$), when signals of different polarity are applied to the inputs 48 and 49 of said multiplier 50. The reason is as follows.

It is known that an increase in the force developed by a working muscle is accompanied by an increase in the amplitude of the time-averaged bioelectric activity of this muscle, as well as by an increase in the mean bioelectric activity frequency of this muscle, and vice versa. However, if the working muscle is tired, for example, at the period of time ($t_1$-$t_2$) under the conditions of a standard load both for static and dynamic work, the amplitude of the time-averaged activity shown in FIG. 13 b increases, whereas its frequency decreases, as shown in FIG. 13 c. The greater the contraction force, the greater the decrease in the frequency. Therefore, if the muscles of the person, whose movements are under control, are tired during the period of time ($t_1$-$t_2$), at the output of the multiplier 50 there is produced a signal shown in FIG. 13 f, which is applied to the control input 56 of the switch 57. From the output of the frequency meter 41 to the input 58 of said switch 57 there is applied a signal shown in FIG. 15 c, which reaches the control input 59 of the voltage divider 60 during the period of time ($t_1$-$t_2$) (FIG. 13 g). To the input 61 (FIG. 6) of the voltage divider 60 there is applied a signal corresponding to the excitation threshold of the muscles being stimulated.

At the output of the voltage divider 60 there is produced an electric signal shown in FIG. 13 h. At the period of time ($t_1$-$t_2$), the amplitude of this signal decreases in accordance with the decrease in the amplitude of the signal applied to the input 59 of the voltage divider 60, i.e. in accordance with the change in the bioelectric activity frequency of the muscles being stimulated.

This signal, corresponding to the excitation threshold of the tired muscles, arrives at the input 30 of the adder 31 and the control input 40 of the voltage divider 38. The process then continues as in the case of the electric stimulator of FIG. 5. At the outputs of the voltage divider 38, the adder 31 and the modulator 9 there are formed signals shown in FIGS. 13 k, l, n, respectively. As a result, during the period of time ($t_1$-$t_2$), when the muscles being stimulated are tired, the amplitude of the converted stimulating signal, which acts on these muscles and is produced at the output of the modulator 9, decreases. The greater the fatigue of the muscles, the greater the decrease in the amplitude. When the fatigue is overcome, the amplitude of this signal returns to the original value.

If the muscles being stimulated are not tired, there is no electric signal at the control input 56 of the switch 57. The signal from the output of the frequency meter 41 does not pass via the switch 57 to the input 59 of the voltage divider 60. Meanwhile, to the input 61 of the voltage divider 60 there is applied an electric signal corresponding to the excitation threshold of the muscles being stimulated. Without a change in its amplitude, this signal proceeds to the input 30 of the adder 31 and the input 40 of the voltage divider 38. Prior to the moment of time $t_1$ or beginning with the moment of time $t_2$, at the outputs of the voltage divider 38, the adder 31 and the modulator 9 there are formed signals shown in FIGS. 13 k, l, n, respectively.

The operation of the stimulator of FIG. 9 is similar to that of the stimulator of FIG. 6. The difference between the two embodiments is as follows.

In each stimulation channel 1 (FIG. 1), the electric signal from the output of the threshold element 33 (FIG. 9) is applied to the input 6 of the comparator 7, the input 37 of the unit 36 and the input of the reference signal setting unit 62 which is a generator of pulses of a standard duration. At the output of said reference signal forming unit 62 there is produced a square pulse of a constant amplitude, which is shown in FIG. 14 a. The leading edge of this pulse coincides in time with the appearance at the output of the integrator 5 of a program signal in the form of the time-averaged bioelectric activity of the person who sets the program of movements. The duration $\tau_4$ of this pulse (FIG. 14 a) is selected to be equal to the maximum possible duration of the pulse formed at the output of the comparator 7 (FIG. 9) and corresponding to the maximum possible excitation threshold of the muscles being stimulated.

The pulse is applied to the input 63 of the threshold element 64, to those input 65 there is applied a pulse from the output of the comparator 7. If the duration of the pulse applied to the input 65 of the threshold element 64 is less than the standard duration of the pulse applied to the input 63, there is no signal at the output of the threshold element 64 and, consequently, at the control input 66 of the switch 67. This indicates that the operating conditions of the stimulation channel 1 (FIG. 1) are normal. The switch 67 (FIG. 9) is closed, and the converted stimulating signal is applied from the output of the modulator 9 to the electrodes 19 connected to the muscles being stimulated.

If the duration $\tau_3$ of the pulse arriving from the output of the comparator 7 is greater than the standard duration, as is shown in FIG. 14 b, i.e. if $\tau_3 > \tau_4$, this indicates that the stimulation channel 1 (FIG. 1) is malfunctioning. At the output of the threshold element 64 (FIG. 9) there is formed a pulse of a constant amplitude, shown in FIG. 14 c. The leading edge of this pulse coincides with the trailing edge of the pulse of a standard duration, shown in FIG. 14 a. From the output of the threshold element 64, this pulse is applied to the control input 66 of the switch. The switch 67 opens so that the converted stimulating signal is not applied from the output of the modulator 9 to the electrodes 19 connected to the muscles being stimulated, whereby these muscles are protected from painful electric signals.

What is claimed is:

1. A bioelectrically controlled electric stimulator of human muscles, comprising:
   an oscillator of the carrier frequency of an electric signal which stimulates muscular activity of a person;
   a group of stimulation channels;
   each of said stimulation channels including:
   a sensor of bioelectric activity of muscles of a person who sets a program of movements; a first integrator connected with its input to the output of said sensor;
   a comparator for comparing bioelectric activity of muscles of the person who sets the program of movements with that of a person whose movements are under control, having first and second inputs;
   the first of said inputs of said comparator being electrically coupled to the output of said first integrator;
   a modulator having first and second inputs;
   said first input of said modulator being connected to the output of said oscillator;
   said second input of said modulator comprising a control input and being electrically coupled to the output of said first integrator through said comparator;
   a power amplifier electrically coupled with its input to the output of said modulator;
   a unit for separating the electric signal, which stimulates the activity of muscles of the person whose movements are under control, from the bioelectric activity of said muscles, caused by said signal, having first and second inputs and first and second outputs;
   the first of said inputs of said separation unit being connected to the output of said power amplifier;
   electrodes adapted to be connected to muscles of the person, whose movements are under control, and also connected to the first of said outputs and the second of said inputs of said separation unit;
   an amplifier of bioelectric activity of muscles of the person whose movements are under control, connected with its input to said second output of said separation unit;
   a second integrator connected with its input to the output of said amplifier of bioelectric activity, the output of said second integrator being electrically coupled to said second input of said comparator.

2. An electric stimulator as claimed in claim 1, wherein each of said stimulation channels further comprises:
   an adder having two inputs, the first being connected to the output of said comparator, while the second is connected to the output of said first integrator, the output of said adder being connected to said control input of said modulator.

3. An electric stimulator as claimed in claim 1, wherein each of said stimulation channels comprises:
   a first threshold element whose input is connected to the output of said first integrator, whereas the output of said first threshold element is connected to the first input of said comparator;
   a second threshold element whose input is connected to the output of said second integrator, whereas its output is connected to said second input of said comparator;
   a unit for forming the excitation threshold of muscles of the person whose movements are under control;
   a first input of said excitation threshold forming unit, connected to the output of said comparator;
   a second input of said excitation threshold forming unit, connected to the output of said first threshold element;
   an adder having two imputs, the first being electrically connected to the output of said excitation threshold forming unit, whereas the second input is electrically connected to the output of said first integrator, the output of said adder being connected to said control input of said modulator.

4. An electric stimulator as claimed in claim 3, wherein each of said stimulation channels comprises:
   a reference signal setting unit connected with its input to the output of said first threshold element;
   a third threshold element;
   a first input of said third threshold element, connected to the output of said reference signal setting unit;
   a second input of said third threshold element, connected to the output of said comparator;
   an electronic switch having a control input connected to the output of said third threshold element, an input connected to the output of said modulator, and an output connected to the input of said power amplifier.

5. An electric stimulator as claimed in claim 3, wherein each of said stimulation channels comprises:
   a first voltage divider having two inputs, the first being connected to the output of said first integrator, whereas the second is electrically coupled to the output of said excitation threshold forming unit, the output of said first voltage divider being connected to said second input of said adder.

6. An electric stimulator as claimed in claim 5, wherein each of said stimulation channels comprises:
- a reference signal setting unit connected with its input to the output of said first threshold element;
- a third threshold element;
- a first input of said third threshold element, connected to the output of said reference signal setting unit;
- a second input of said third threshold element, connected to the output of said comparator;
- an electronic switch having a control input connected to the output of said third threshold element, an input connected to the output of said modulator, and an output connected to the input of said power amplifier.

7. An electric stimulator as claimed in claim 5, wherein each of said stimulation channels comprises:
- a frequency meter connected with its input to the output of said bioelectric activity amplifier;
- a first differentiator amplifier connected with its input to the output of said frequency meter;
- a second differentiator amplifier connected with its input to the output of said second integrator;
- a multiplier;
- a first input of said multiplier, connected to the output of said first differentiator amplifier;
- a second input of said multiplier, connected to the output of said second differentiator amplifier;
- a first electronic switch;
- an input of said first electronic switch, connected to the output of said frequency meter;
- a control input of said electronic switch, connected to the output of said multiplier;
- a second voltage divider having two inputs, the first being connected to the output of said first electronic switch, whereas the second is connected to the output of said excitation threshold forming unit, the output of said second voltage divider being connected to said first input of said adder.

8. An electric stimulator as claimed in claim 7, wherein each of said stimulation channels comprises:
- a reference signal setting unit connected with its input to the output of said first threshold element;
- a third threshold element;
- a first input of said third threshold element, connected to the output of said reference signal setting unit;
- a second input of said thrid threshold element, connected to the output of said comparator;
- a second electronic switch having a control input connected to the output of said third threshold element, an input connected to the output of said modulator, and an output connected to the input of said power amplifier.

* * * * *